US006331547B1

(12) United States Patent
Zhu et al.

(10) Patent No.: US 6,331,547 B1
(45) Date of Patent: Dec. 18, 2001

(54) WATER SOLUBLE SDZ RAD ESTERS

(75) Inventors: Tianmin Zhu, Monroe, NY (US); Syed M. Shah, East Hanover, NJ (US); Richard W. Saunders, Palisades, NY (US)

(73) Assignee: American Home Products Corporation, Madison, NJ (US)

(*) Notice: Subject to any disclaimer, the term of this patent is extended or adjusted under 35 U.S.C. 154(b) by 0 days.

(21) Appl. No.: 09/639,610

(22) Filed: Aug. 16, 2000

Related U.S. Application Data

(60) Provisional application No. 60/183,035, filed on Aug. 18, 1999.

(51) Int. Cl.$^7$ .................. C07D 498/16; C07D 498/18; C07D 491/06; A61K 31/395; A61K 31/445
(52) U.S. Cl. ............................ 514/291; 540/456
(58) Field of Search ................. 514/291; 540/456

(56) References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,401,653 | 8/1983 | Eng | 424/114 |
| 4,650,803 | 3/1987 | Stella et al. | 514/291 |
| 4,684,728 | 8/1987 | Mohring et al. | 544/182 |
| 4,885,171 | 12/1989 | Surendra et al. | 424/122 |
| 5,023,263 | 6/1991 | Von Burg | 514/291 |
| 5,023,264 | 6/1991 | Caufield et al. | 514/291 |
| 5,078,999 | 1/1992 | Warner et al. | 424/122 |
| 5,080,899 | 1/1992 | Sturm et al. | 424/122 |
| 5,100,883 | 3/1992 | Schiehser | 514/183 |
| 5,100,899 | 3/1992 | Calne | 514/291 |
| 5,118,677 | 6/1992 | Caufield | 514/183 |
| 5,118,678 | 6/1992 | Kao et al. | 514/183 |
| 5,120,842 | 6/1992 | Failli et al. | 540/452 |
| 5,130,307 | 7/1992 | Failli et al. | 514/321 |
| 5,151,413 | 9/1992 | Caufield et al. | 514/63 |
| 5,162,333 | 11/1992 | Failli et al. | 514/291 |
| 5,177,203 | 1/1993 | Failli et al. | 540/456 |
| 5,221,670 | 6/1993 | Caufield | 514/183 |
| 5,233,036 | 8/1993 | Hughes | 540/455 |
| 5,258,389 | 11/1993 | Goulet et al. | 514/291 |
| 5,260,300 | 11/1993 | Hu | 514/291 |
| 5,262,423 | 11/1993 | Kao | 514/291 |
| 5,302,584 | 4/1994 | Kao et al. | 514/80 |
| 5,362,718 | 11/1994 | Skotnicki et al. | 514/63 |
| 5,385,908 | 1/1995 | Nelson et al. | 514/291 |
| 5,385,909 | 1/1995 | Nelson et al. | 514/291 |
| 5,385,910 | 1/1995 | Ocain et al. | 514/291 |
| 5,387,680 | 2/1995 | Nelson | 540/456 |
| 5,389,639 | 2/1995 | Failli et al. | 514/291 |
| 5,391,730 | 2/1995 | Skotnicki et al. | 540/456 |
| 5,411,967 | 5/1995 | Kao et al. | 514/291 |
| 5,434,260 | 7/1995 | Skotnicki et al. | 514/291 |
| 5,463,048 | 10/1995 | Skotnicki et al. | 540/456 |
| 5,480,988 | 1/1996 | Failli et al. | 540/456 |
| 5,480,989 | 1/1996 | Kao et al. | 540/456 |
| 5,489,680 | 2/1996 | Failli et al. | 540/456 |
| 5,491,231 | 2/1996 | Nelson et al. | 540/456 |
| 5,504,091 | 4/1996 | Molnar-Kimber et al. | 514/291 |
| 5,563,145 | 10/1996 | Failli et al. | 514/291 |
| 5,665,772 | 9/1997 | Cottens et al. | 514/514 |
| 5,780,462 | 7/1998 | Lee et al. | 514/183 |
| 5,985,890 | 11/1999 | Cottens et al. | 514/291 |
| 6,015,809 | 1/2000 | Zhu et al. | 514/210 |

FOREIGN PATENT DOCUMENTS

| | | |
|---|---|---|
| 0525960 | 2/1993 | (EP). |
| 0532862 | 3/1993 | (EP). |
| 9409010 | 4/1994 | (WO). |

OTHER PUBLICATIONS

Zalipsky et al., Eur. Polymer Journal, 19(12), 1983, 1177–1183.
Crowe and Lemaire, Pharmaceutical Research, 1998, 15(11), 1666–1672.
Sehgal et al., J. Antibiot., 1975, 28, 727.
Baker et al., J. Antibiot., 1978, 31, 539.
Vezina et al., J. Antibiot., 1975, 28, 721.
Morris, R. J. Heart Lung Transplant, 1992, 11(1) pt. 2, 197.
Baeder et al., 5$^{th}$ Intl' Conference of Inflammation Res. Assoc. 121 (Abstract), 1990.
Martel et al., Can. J. Physiol. Pharmacol., 1997, 55, 48.
Staruch et al. FASEB, 1989, 3(3), 3411.
Dumont et al., FASEB, 1989, 3(4), 5256.
Calne et al., Lancet, 1978, 1183.

*Primary Examiner*—Bruck Kifle
(74) *Attorney, Agent, or Firm*—Arnold S. Milowsky

(57) ABSTRACT

This invention provides novel water soluble pegylated esters of rapamycin, having the general structure:

wherein n is an integer from about 5 to about 450, as well as pharmaceutical compositions containing these compounds and methods for their use as immunosuppressive, anti-inflammatory, antifungal, antiproliferative and antitumor agents.

18 Claims, No Drawings

WATER SOLUBLE SDZ RAD ESTERS

This application claims the benefit of U.S. Provisional Application No. 60/183,035, which was converted from U.S. patent application Ser. No. 09/376,685, filed Aug. 18, 1999, pursuant to a petition filed under 37 C.F.R. 1.53(c)(2)(i).

BACKGROUND OF THE INVENTION

This invention relates to water soluble SDZ-RAD esters, methods for its preparation and methods for its use for inducing immunosuppression and in the treatment of transplantation rejection, autoimmune diseases, solid tumors. More particularly, this invention concerns pegylated esters of SDZ-RAD and methods for using them for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

SDZ-RAD is 40-O-(2-hydroxy)ethyl-rapamycin, the structure and synthesis of which is disclosed in WO 94/09010 (Cottens et al.).

Authors Crowe and Lemaire describe the in vitro and in situ absorption of SDZ-RAD, an analog of rapamycin having the structure:

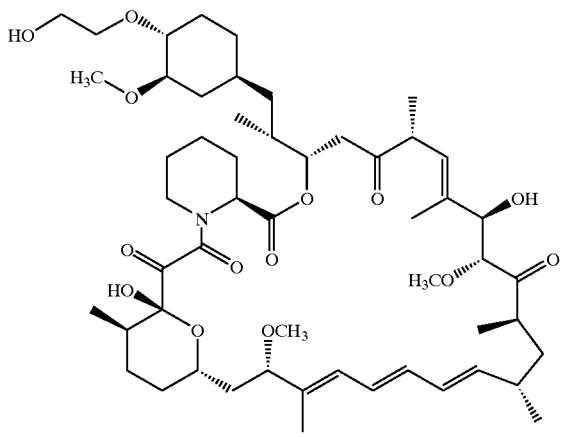

in their article in Pharmaceutical Research, Vol. 15, No. 11, 1998

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,023,263 describes the preparation and use of 42-oxorapamycin and U.S. Pat. No. 5,023,264 describes the preparation and use of 27-oximes of rapamycin.

Polyethylene glycol (PEG) is a linear or branched, neutral polymer available in a variety of molecular weights and is soluble in water and most organic solvents. At molecular weights less than 1000 PEGs are the viscous, colorless liquids; higher molecular weight PEGs are waxy, white solids. The melting point of the solid is proportional to the molecular weight, approaching a plateau at 67° C. Molecular weights range from a few hundred to approximately 20,000 are commonly used in biological and biotechnological applications. Of much interest in the biomedical areas is the fact that PEG is nontoxic and was approved by FDA for internal consumption.

SDZ-RAD is a rapamycin derivative which has immunosuppressive activity in animal model (U.S. Pat. No. 5,665,772). U.S. Pat. No. 5,665,772 (Cottens et al.) teaches O-alkylated rapamycin derivatives, particularly 9-deoxorapamycins, 26-dihydro-rapamycins, 40-O-substituted rapamycins and 28,40-O,O-disubstituted rapamycins. It is known that pegylated rapamycin is an ester derivative which shows immunosuppressive activity with improved aqueous solubility (U.S. Pat. No. 5,780,462). Using the similar synthetic method, water soluble derivatives of SDZ-RAD has been prepared.

DESCRIPTION OF THE INVENTION

This invention provides novel polyethylene glycol esters of SDZ-RAD, an analog of rapamycin, which are compounds of the formula:

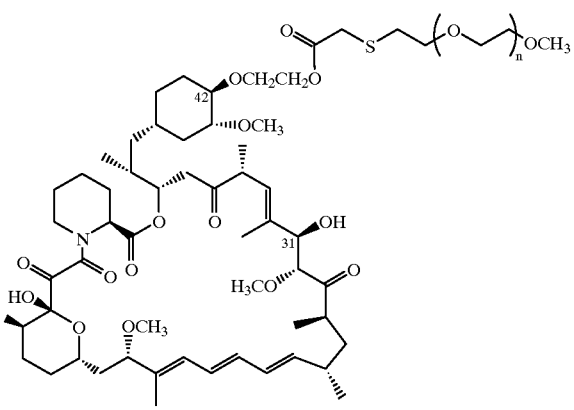

wherein n is an integer from about 5 to about 450.

The compounds of this invention are water soluble analogs of SDZ-RAD and rapamycin which are useful as immunosuppressive, antiinflammatory, antifungal, antiproliferative, and antitumor agents. Of the compounds of this invention, it is preferred that n=5–200; more preferred that n=8–135. Most preferred members are those in which n=8–20 and those in which n=90–120. The compounds of this invention may also be described and understood based upon the average molecular weight of the polyethylene glycol chains used to produce their ester chains. For instance, an SDZ-RAD-PEG-5000 conjugate ester refers to a compound of the general formula above in which the 42-O-(2-Hydroxy)-ethyl position ester is formed utilizing a polyethylene glycol derivative having an average molecular weight range at or near 5,000.

The esters of the present invention may be produced utilizing the polyethylene glycols known in the art, such as those described on pages 355 to 361 of the Handbook of Pharmaceutical Excipients, Second Edition, 1994 (Library of Congress Catalog Card No. 94-79492), which are incorporated herein by reference. The preferred compounds of this invention may also be described as those of the formula esterified using polyethylene glycols having an average molecular weight of from about 200 to about 200,000. A preferred range of the PEG esters of this invention includes those in which the molecular weight of the polyethylene glycol portion of the ester chain has a molecular weight in the range of from about 300 to about 20,000, more preferably between about 350 and about 6,000. Non-limiting specific examples of compounds of this invention include compounds of the formula above prepared using each of the PEGs listed in the Handbook of Pharmaceutical Excipients, Second Edition, 1994.

The compounds are useful in treating, preventing or inhibiting conditions for which rapamycin, its analogs and prodrugs may be used. These methods include the treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Because of the activity profile obtained, the compounds of this invention also are considered to have antitumor, antifungal activities, and antiproliferative activities. The compounds of this invention therefore also useful in treating solid tumors, including sarcomas and carcinomas, such as astrocytomas, prostate cancer, breast cancer, small cell lung cancer, and ovarian cancer; adult T-cell leukemia/lymphoma; fungal infections; and hyperproliferative vascular diseases such as restenosis and atherosclerosis. When used for restenosis, it is preferred that the compounds of this invention are used to treat restenosis that occurs following an angioplasty procedure. When used for this purpose, the compounds of this invention can be administered prior to the procedure, during the procedure, subsequent to the procedure, or any combination of the above.

When administered for the treatment or inhibition of the above disease states, the compounds of this invention can be administered to a mammal orally, parenterally, intranasally, intrabronchially, transdermally, topically, intravaginally, or rectally.

The compounds of this invention are particularly advantageous as immunosuppressive, antiinflammatory, antifungal, antiproliferative, and antitumor agents because of their water solubility.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

This invention also comprises pharmaceutical compositions comprising one or more of the PEG esters of this invention and one or more pharmaceutically acceptable carriers or excipients. The pharmaceutical carriers or excipients may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 μg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The 42-O-(2-Hydroxy)ethyl on SDZ-RAD esterified compound of this invention can be prepared by initially acylating the hydroxyl group on 42-O-(2-Hydroxy)ethyl or 31-position or both position of SDZ-RAD with an acylating agent having the general structure X—CH$_2$CO$_2$H, where X is a suitable leaving group such as iodine or bromine, in the presence of a coupling reagent, such as dicyclohexlcarbodiimide (DCC) and a base catalyst such as dimethylaminopyridine (DMAP) to provide either a 42-O-(2-Hydroxy) ethyl and/or 31-hydroxy acylated SDZ-RAD having the following structure where R$^1$ and R$^2$ are independently from —H and —COCH$_2$X.

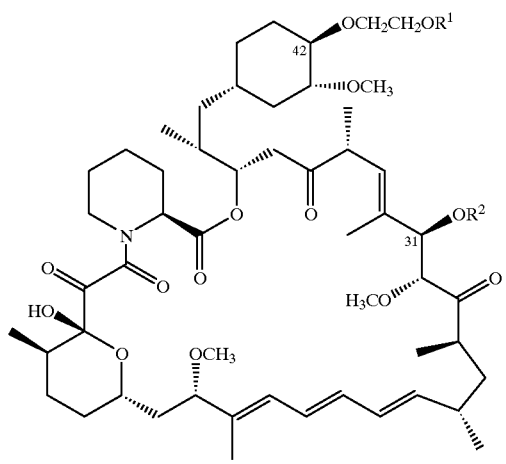

Every possible compound can be separated by chromatography. Reaction of the acylated SDZ-RAD with monomethoxypoly(ethylene glycol) thiol in the presence of base such as sodium bicarbonate provides the desired ester on 42-O-(2-Hydroxy)ethyl of SDZ-RAD of this invention. This novel method can be applied to any hydroxyalkyl, dihydroxyalkyl, hydroalkylarylalkyl, dihydroalkylarylalkyl, dihydroxyalkylally derivative of rapamycin in U.S. Pat, No. 5,665,772.

The preparation of rapamycin 42-silyl ethers is described in U.S. Pat. No. B1 5,120,842, which is hereby incorporated by reference. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

This invention also covers analogous esters of other rapamycins known in the art such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023, 262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; 27-hydroxyrapamycin [U.S. Pat. No. 5,256,790] and 15-hydroxyrapamycin [U.S. Pat. No. 5,102,876]. This invention also covers esters at the 31-position of 42-oxorapamycin [U.S. Pat. No. 5,023,263]. The disclosures in the above cited U.S. Patents are hereby incorporated by reference.

The reagents used in the preparation of the compounds of this invention can be either commercially obtained or can be prepared by standard procedures described in the literature.

The following examples illustrate the preparation and biological activities of representative compounds of this invention.

EXPERIMENTAL SECTION

Material and Instruments 1,3-Dicyclohexylcarbodiimide (DCC) and 4-dimethylaminopyridine were purchased from Aldrich Chemical Co. (Milwaukee, Wis.). Methoxy-PEG-SH of average molecular weight 5000 (mPEG-SH 5000) was purchased from Shearwater Polymers, Inc. (Huntsville, Ala.). SDZ-RAD was obtained from Chemical Development Wyeth-Ayerst Research, Pearl River, N.Y. All solvents were HPLC grade and all other chemicals were analytical reagent or equivalent. The preparative HPLC consisted of two Dynamax solvent delivery systems (Model SD-1) and one Dynamax absorbance detector (Model UV-1) from Rainin Instrument Inc.(Woburn, Mass.). An automatic speed-vac concentrator (Savant, Model AS 160) was from Savant Instruments, Inc. (Holbrook, N.Y.) and a BUCHI rotary evaporation system (RE 260 and R 124) was from Buchi (Flawil, Switzerland). $^1$H-NMR spectra were recorded on 400 MHz NMR spectrophotometer using $CDCl_3$ as solvents. Mass spectra were obtained from API 365 mass spectrophotometer or MALDI/TOF mass spectrophotometer from PE Sciex. All samples were prepared and run at ambient temperature.

HPLC Method

The analytical HPLC system consisted of a Hewlett-Packard model 1090 LC with a 1040 diode array detector system. A $\mu$-Bondapak C-18 (300×3.9 mm) column from Waters was used. The mobile phase A was 10% acetonitrile, 90% 0.1 M 0.1 M tetraethylammonium acetate (TEAA) buffer at pH 4.5. The mobile phase B was 90% acetonitrile, 10% 0.1 M TEAA buffer at pH 4.5. The gradient was from 50% B to 100% B in 30 min then held 100% B for 5 min before going beck original 50% B. The column was equilibrated at 50% B for 15 min before next injection. The column temperature was 40° C. and flow rate was 1 mL/min. The detection wavelength was set at 280 nm. The injection volume was 10 μl.

Preparation of SDZ-RAD-iodoacetate ester

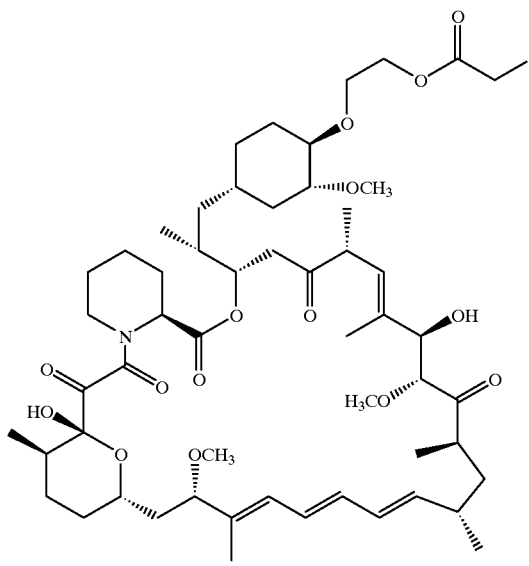

SDZ-RAD (0.50 g 5.2×10$^{-4}$ mole), 4-Dimethylaminopyridine (3.0 mg) and 1,3-Dicyclohexylcarbodiimide (0.136 g, 6.6×10$^{-4}$ mole) were dissolved in 20 ml anhydrous methylene chloride in a 150 ml round-bottom flask. Iodoacetic acid (0.116 g, 6.3×10$^{-4}$ mole) was dissolved in 10 ml anhydrous methylene chloride. The iodoacetic acid solution was added into the reaction mixture over a period of 10 min. with stirring by a magnetic bar. Then the reaction mixture was stirred at room temperature for another 2.5 h. The solution was then filtered through a sintered glass filter. The filtrate was transferred to a separatory funnel, washed 50 ml of sodium bicarbonate solution (5.5 g/100 ml) and then washed with 2×50 ml of water. The methylene chloride layer was dried with 5 g anhydrous sodium sulfate for 4 h. Then sodium sulfate was filtered out and methylene chloride was removed by rotary evaporation. A total of 0.60 g pale yellow solid was obtained. Isolation of pure SDZ-RAD-iodoacetate ester was performed by preparative HPLC on a Prep Nova-pak HR C18 (300×19 mm) column from Waters. SDZ-RAD-iodoacetate ester eluted at 18.4 min using a gradient (30% A, 70% B for 5 min. then to 100% B in 30 min.). A is 90% water, 10% acetonitrile; B is 10% water, 90% acetonitrile. The fraction was collected and extracted by 2×50 ml methylene chloride. The organic layer was combined and dried with anhydrous sodium sulfate for 4 h. The organic solvent was removed by rotary evaporation to dryness. A yellowish solid was obtained (0.102 g). $^1$H NMR ($CDCL_3$, 400 MHz) d 3.72 (s, 2H, I—C$\underline{H}_2$—$CO_2$—), 4.28 (m, 2H, —$CO_2$—C$\underline{H}_2$—). MS m/z 1134.6 $(M+NH_4)^+$; m/z 1184.6 $(M+OAc)^-$. MS/MS 213.0 $(ICH_2CO_2CH_2CH_2)^+$.

Preparation of SDZ-RAD-PEG 5000 conjugate

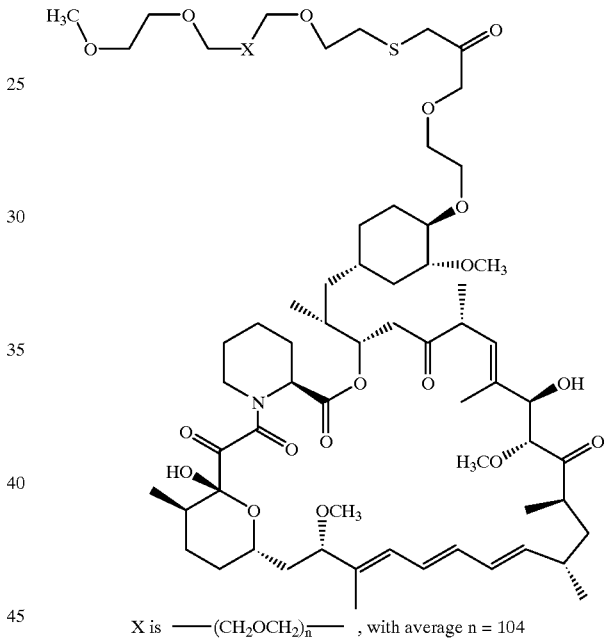

X is ——$(CH_2OCH_2)_n$—— , with average n = 104

SDZ-RAD iodoacetate ester (76 mg, 6.8×10$^{-5}$ mole) was dissolved in 30 ml of solution containing 50% acetonitrile and 50% aqueous $NaHCO_3$ (0.1 M) solution. The solution was flushed with $N_2$ for 10 min. The original sample 10 μL was taken for HPLC analysis. Then mPEG-SH 5000 (337 mg, 6.8×10$^{-5}$ mole) was added to the reaction solution and the reaction mixture was stirred at room temperature for another 30 min. The reaction was checked again by taking 10 μL sample for HPLC analysis. The chromatogram showed that SDZ-RAD iodoacetate ester was 100% converted to SDZ-RAD-PEG conjugate. The reaction mixture was extracted with 2×150 ml methylene chloride. The organic layer was dried with anhydrous sodium sulfate then filtered. The filtrate was concentrated to a volume of 20 ml by rotaty evaporation. The crude product was precipitated out after adding 200 mLether. A total of 340 mg pale yellow powder was obtained after filtered out by a sintered glass funnel and dried under vacuum. Isolation of pure SDZ-RAD-PEG conjugate, which may also be referred to as pegylated SDZ-RAD, was performed by preparative HPLC on a Prep Nova-pak HR C18 (300×19 mm) column from Waters. SDZ-RAD-iodoacetate ester eluted at 15 min. using a gradient (60% A, 40% B for 5 min. then at 20% A, 80% B in 30 min.) The fraction was collected and extracted by 2×100 ml methylene chloride. The organic layer was combined and dried with anhydrous sodium sulfate for 4 hr. The organic solvent was removed by rotary evaporation to dryness. The residue was dissolved in 5 ml methylene chloride and was precipitated out after adding 150 ml ether. A pale yellow powder was obtained after filtered out by a sintered glass funnel and dried under vacuum. $^1$H NMR (CDCl$_3$, 400 MHz) δ 2.84 (t, 2H, S—CH$_2$—CH$_2$), 3.31 (s, 2H, CO—CH$_2$—S), 3.38 (s, 3H, —OCH$_3$), 4.26 (m, 2H, —CO$_2$—CH$_2$—). MS (MALD/TOF) m/z 5795.5.

U87MG Human Glioblastoma (ATCC # HTB-14)

3H Thymidine Incorporation Protocol

Growth Medium:

BRL Minimum Essential Medium with Earle Salts (500 ml)
+5 mLBRL MEM Non-Essential Amino Acids (10 mM)
+5 mLBRL Penicillin-Streptomycin
   (10000 u/ml,10000 ug/ml)
+5 mLBRL Na Pyruvate Solution (100 mM)
+5 mLBRL L-Glutamine 200 mM
+50 mLBRL Fetal Bovine Serum (Qualified)

Assay:

1. Cells were trypsinized and plated at a concentration of 10$^4$ cells/well in a final volume of 200 μl growth medium in 96-well flat bottom plates and allowed to adhere for 24 hours at 37° C.
2. The media was removed by aspiration with care to not disturb the cell monolayer. 200 μl of fresh growth media was added per well, allowing enough wells for samples to be run in triplicate. Compounds were added in 10 μl PBS solutions and incubated for another 48 hours at 37° C.
3. During the last 5 hours of incubation, plates were labeled with 1 μCi 3H thymidine per well. (NEN thymidine, catalog # NET-027, 6.7 Ci/mmole). The 1 μCi was added in 10 μl of PBS (on the day of harvest.). The plates were returned to the incubator for the last 5 hours.
4. The radioactive media was removed by aspiration, with care not to disturb the cell monolayer. 50 μl of BRL 10×Trypsin was added to each well, followed by incubation at 37° C. for 10 minutes or until the monolayer was loosened from the well bottom. Samples were harvested on a glass fiber filter mat using a Skatron 96 well harvester. Mats were counted in a Wallac Betaplate counter.

| Results | |
|---|---|
| Compound | IC$_{50}$ |
| Rapamycin | 0.5 ng/mL |
| SDZ-RAD | 2.0 ng/mL |
| SDZ-RAD-PEG 5000 conjugate | 0.5 ng/mL* |

*equivalent to SDZ-RAD

What is claimed:

1. A compound of the structure

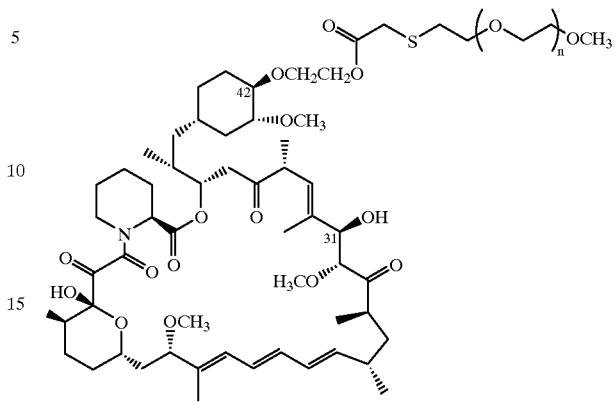

wherein n is an integer from 5–450.

2. The compound of claim 1 wherein n=5–200.

3. The compound of claim 1 wherein n=8–135.

4. The compound of claim 1 wherein n=8–20.

5. The compound of claim 1 wherein n=90–120.

6. The compound of claim 1 which is SDZ-RAD-PEG 5000 conjugate.

7. A method of treating transplantation rejection or graft vs. host disease in a mammal in need thereof, which comprises administering to said mammal an antirejection effective amount of a compound of the structure

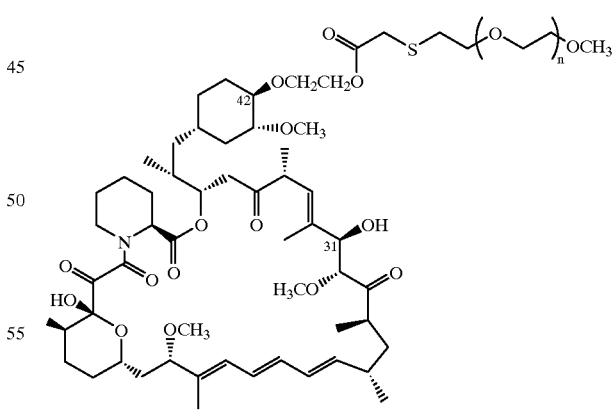

wherein n is an integer from 5–450.

8. A method of treating a fungal infection in a mammal in need thereof, which comprises administering to said mammal an antifungal effective amount of a compound of the structure

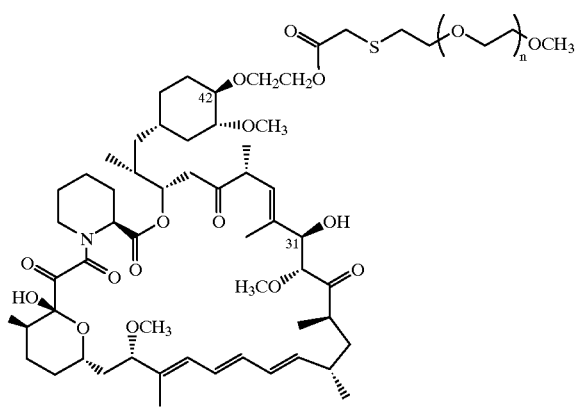

wherein n is an integer from 5–450.

9. A method of treating rheumatoid arthritis in a mammal in need thereof, which comprises administering to said mammal an antiarthritis effective amount of a compound of the structure

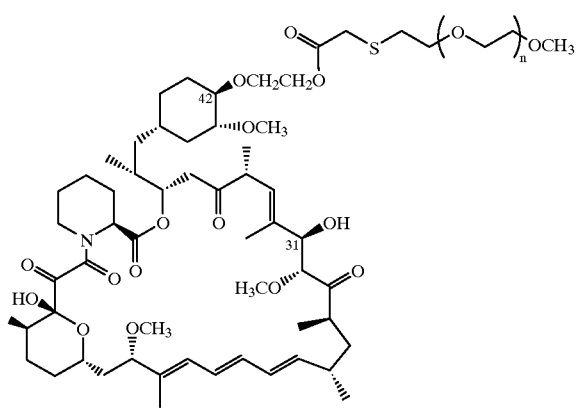

wherein n is an integer from 5–450.

10. A method of treating restenosis in a mammal in need thereof, which comprises administering to said mammal an antiproliferative effective amount of a compound of the structure

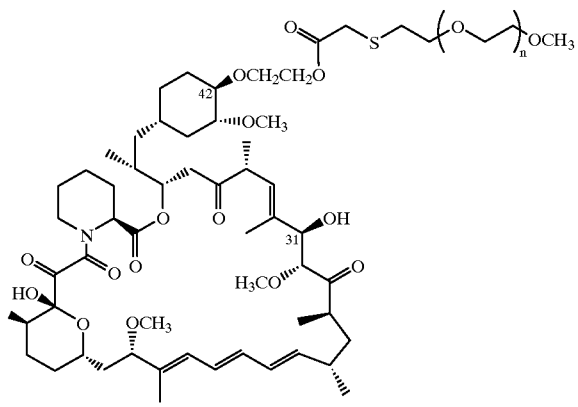

wherein n is an integer from 5–450.

11. A method of treating pulmonary inflammation in a mammal in need thereof, which comprises administering to said mammal an antiinflammatory effective amount of a compound of the structure

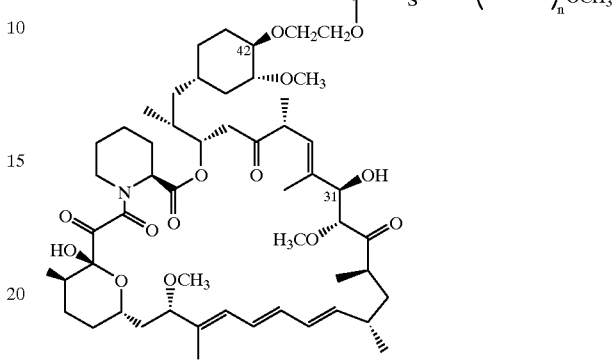

wherein n is an integer from 5–450.

12. A pharmaceutical composition which comprises a compound of the structure

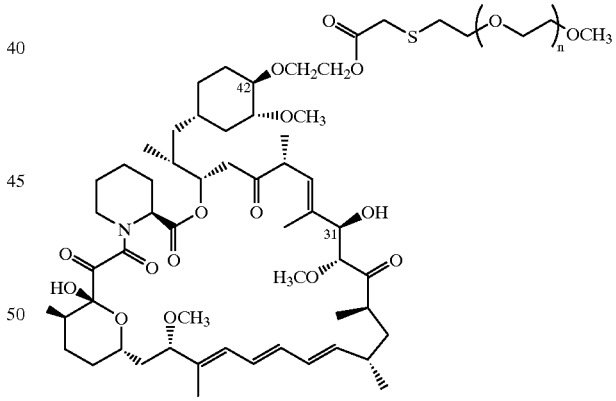

wherein n is an integer from 5–450, and a pharmaceutically acceptable carrier or excipient.

13. The pharmaceutical composition of claim 12 wherein n=8–200.

14. The pharmaceutical composition of claim 12 wherein n=8–135.

15. The pharmaceutical composition of claim 12 wherein n=8–20.

16. The pharmaceutical composition of claim 12 wherein n=90–120.

17. The pharmaceutical composition of claim 12 which is SDZ-RAD-PEG 5000 conjugate.

18. A method of treating glioblastoma in a mammal in need thereof, which comprises administering to said mammal an effective amount of a compound of the structure

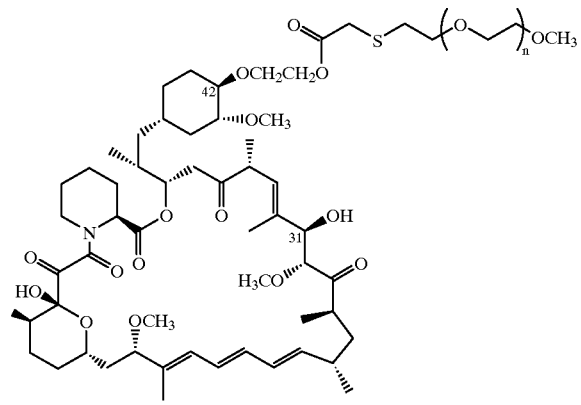

wherein n is an integer from 5–450.

* * * * *